United States Patent
Tsai et al.

(10) Patent No.: US 9,399,048 B2
(45) Date of Patent: Jul. 26, 2016

(54) LACTIC ACID BACTERIA AND ITS APPLICATIONS IN IMMUNOMODULATION AND ANTI-INFLAMMATION

(71) Applicant: ASIAN PROBIOTICS AND PREBIOTICS LTD., Mahe (SC)

(72) Inventors: Ying-Chieh Tsai, Taipei (TW); Chien-Chen Wu, Taipei (TW); Jian-Fu Liao, Taipei (TW)

(73) Assignee: ASIAN PROBIOTICS AND PREBIOTICS LTD, Mahe (SC)

( * ) Notice: Subject to any disclaimer, the term of this patent is extended or adjusted under 35 U.S.C. 154(b) by 0 days.

(21) Appl. No.: 14/198,020

(22) Filed: Mar. 5, 2014

(65) Prior Publication Data

US 2015/0250834 A1    Sep. 10, 2015

(51) Int. Cl.
| | |
|---|---|
| *A61K 39/02* | (2006.01) |
| *A61K 35/747* | (2015.01) |
| *A23L 1/30* | (2006.01) |
| *A23L 2/52* | (2006.01) |
| *A61K 39/09* | (2006.01) |
| *C12R 1/25* | (2006.01) |

(52) U.S. Cl.
CPC ............. *A61K 35/747* (2013.01); *A23L 1/3014* (2013.01); *A23L 2/52* (2013.01); *A61K 39/09* (2013.01); *C12R 1/25* (2013.01); *A23V 2002/00* (2013.01); *A23Y 2220/67* (2013.01)

(58) Field of Classification Search
None
See application file for complete search history.

(56) References Cited

PUBLICATIONS

Office Action and Search Report dated May 25, 2015 for counterpart Taiwan application No. 103107518.
English translation of the Search Report dated May 25, 2015 for counterpart Taiwan application No. 103107518.
Liu, Yen-Wenn et al., "Oral Administration of Lactobacillus plantarum K68 Ameliorates DSS-induced Ulcerative Colitis in BALB/c Mice via the Anti-Inflammatory and Immunomodulatory Activities", International Immunopharmacology, 2011, vol. 11, Issue 13, p. 2159-2166.

*Primary Examiner* — J. Hines
*Assistant Examiner* — Khatol Shahnan Shah
(74) *Attorney, Agent, or Firm* — WPAT, P.C., Intellectual Property Attorneys; Anthony King

(57) ABSTRACT

The invention provides a new lactic acid bacteria (LAB) strain with immunomodulatory and anti-inflammatory activity and a composition containing and method using the same. The LAB of the invention can be administrated for modulating an immune response in order to restore or prevent metabolic disorders caused by obesity or chronic inflammation.

9 Claims, 5 Drawing Sheets

SEQUENCE LISTING

<160> NUMBER OF SEQ ID NOS: 19

<210> SEQ ID NO 1
<211> LENGTH: 1119
<212> TYPE: DNA
<213> ORGANISM: Lactobacillus plantarum

<400> SEQUENCE: 1
ggagactata catgcaagtc gaacgaactc tggtattgat tggtgcttgc atcatgattt     60
acatttgagt gagtggcgaa ctggtgagta acacgtggga aacctgccca gaagcggggg    120

```
ataacacctg gaaacagatg ctaataccgc ataacaactt ggaccgcatg gtccgagttt    180
gaaagatggc ttcggctatc acttttggat ggtcccgcgg cgtattagct agatggtggg    240
gtaacggctc accatggcaa tgatacgtag ccgacctgag agggtaatcg ccacattgg     300 gactgagaca cggcccaaac tcctacggga ggcagcagta gggaatcttc cacaatggac    360
gaaagtctga tggagcaacg ccgcgtgagt gaagaagggt ttcggctcgt aaaactctgt    420
tgttaaagaa gaacatatct gagagtaact gttcaggtat tgacggtatt taaccagaaa    480
gccacggcta actacgtgcc agcagccgcg gtaatacgta ggtggcaagc gttgtccgga    540
tttattgggc gtaaagcgag cgcaggcggt tttttaagtc tgatgtgaaa gccttcggct    600
caaccgaaga agtgcatcgg aaactgggaa acttgagtgc agaagaggac agtggaactc    660
cgtgtgtagc ggtgaaatgc gtagatatat ggaagaacac cagtggcgaa ggcggctgtc    720
tggtctgtaa ctgacgctga tgctcgaaag tatgggtagc aaacaggatt agataccctg    780
gtagtccata ccgtaacgat gaatgctaag tgttggaggg tttccgccct tcagtgctgc    840
agctaacgca ttaagcattc cgcctgggga gtacggcgca ggctgaaact cagaggaatt    900
gacgggggtc ccgcacaagc ggtgcagcat gtgtttattc gaagctacgc gaagatctac    960
aggtctgaca tactatgcaa atctagaaat aacgttcttt cgtgacatgc atacagtgtg   1020
catggtgtcg tcagtcagtt cctgatgtcg attagttcaa gacgaggcac ctactatcag   1080
tgccagcata gtggcatctg tgagactgcc gtgacaaac                          1119

<210> SEQ ID NO 2
<211> LENGTH: 473
<212> TYPE: DNA
<213> ORGANISM: Lactobacillus plantarum

<400> SEQUENCE: 2
tgcgaatatt accaagacgt gctactacgc acgcagacgt ctgctgatca gccgcggtca     60
cttgaaaatc acgattttc taaaggaccg ctgaaggtct tgtcacctgg ccgcgtttat    120
cggcgtgata cggatgatgc aacccattcc catcaatttc atcaaattga agggttagtc    180
gtggacaagc atattacgat ggctgatttg aagggcacct taattctggt tgccaagact    240
ttgtttggcg atcaattcga tgttcggcta cggccaagct tctttccatt cacggaacca    300
tccgtagaag ctgatgtaac ttgctttaat tgcaatggca agggctgtgc aatctgtaag    360
caaacgggtt ggatcgaagt actgggtgcc ggcatggttc accccacgt gttagaaatg    420 tctggcattg atccagaaga atatggtggc tttgctttcg gggtcttgga aca           473

<210> SEQ ID NO 3
<211> LENGTH: 20
<212> TYPE: DNA
<213> ORGANISM: Artificial Sequence
<220> FEATURE:
<223> OTHER INFORMATION: Synthesized primer

<400> SEQUENCE: 3
agagtttgat cmtggctcag                                                20

<210> SEQ ID NO 4
<211> LENGTH: 20
<212> TYPE: DNA
<213> ORGANISM: Artificial Sequence
<220> FEATURE:
<223> OTHER INFORMATION: Synthesized primer

<400> SEQUENCE: 4
```
aaggaggtga tccaaccgca                                          20

<210> SEQ ID NO 5
<211> LENGTH: 19
<212> TYPE: DNA
<213> ORGANISM: Artificial Sequence
<220> FEATURE:
<223> OTHER INFORMATION: Synthesized primer
<220> FEATURE:
<221> NAME/KEY: misc_feature
<222> LOCATION: (6)..(6)
<223> OTHER INFORMATION: n is a, c, g, or t

<400> SEQUENCE: 5
cayccngchc gygayatgc                                           19

<210> SEQ ID NO 6
<211> LENGTH: 20
<212> TYPE: DNA
<213> ORGANISM: Artificial Sequence
<220> FEATURE:
<223> OTHER INFORMATION: Synthesized primer

<400> SEQUENCE: 6
ccwarvccra argcaaarcc                                          20

<210> SEQ ID NO 7
<211> LENGTH: 10
<212> TYPE: DNA
<213> ORGANISM: Artificial Sequence
<220> FEATURE:
<223> OTHER INFORMATION: Synthesized primer

<400> SEQUENCE: 7
ccgcagccaa                                                     10

<210> SEQ ID NO 8
<211> LENGTH: 20
<212> TYPE: DNA
<213> ORGANISM: Artificial Sequence
<220> FEATURE:
<223> OTHER INFORMATION: Synthesized primer

<400> SEQUENCE: 8
gtggaactgg cagaagaggc                                          20

<210> SEQ ID NO 9
<211> LENGTH: 20
<212> TYPE: DNA
<213> ORGANISM: Artificial Sequence
<220> FEATURE:
<223> OTHER INFORMATION: Synthesized primer

<400> SEQUENCE: 9
agacagaaga gcgtggtggc                                          20

<210> SEQ ID NO 10
<211> LENGTH: 20
<212> TYPE: DNA
<213> ORGANISM: Artificial Sequence
<220> FEATURE:
<223> OTHER INFORMATION: Synthesized primer

<400> SEQUENCE: 10
aggagtgccc cgctttcacc                                          20

```
<210> SEQ ID NO 11
<211> LENGTH: 19
<212> TYPE: DNA
<213> ORGANISM: Artificial Sequence
<220> FEATURE:
<223> OTHER INFORMATION: Synthesized primer

<400> SEQUENCE: 11
tgccagagcg gctgccaga                                                  19

<210> SEQ ID NO 12
<211> LENGTH: 22
<212> TYPE: DNA
<213> ORGANISM: Artificial Sequence
<220> FEATURE:
<223> OTHER INFORMATION: Synthesized primer

<400> SEQUENCE: 12
gaagtctttg gtctggtgcc tg                                              22

<210> SEQ ID NO 13
<211> LENGTH: 23
<212> TYPE: DNA
<213> ORGANISM: Artificial Sequence
<220> FEATURE:
<223> OTHER INFORMATION: Synthesized primer

<400> SEQUENCE: 13
gtctgctggt ttggaatagt tgc                                             23

<210> SEQ ID NO 14
<211> LENGTH: 23
<212> TYPE: DNA
<213> ORGANISM: Artificial Sequence
<220> FEATURE:
<223> OTHER INFORMATION: Synthesized primer

<400> SEQUENCE: 14
tgcagggcag ctaggtactt gta                                             23

<210> SEQ ID NO 15
<211> LENGTH: 21
<212> TYPE: DNA
<213> ORGANISM: Artificial Sequence
<220> FEATURE:
<223> OTHER INFORMATION: Synthesized primer

<400> SEQUENCE: 15
tctcggagat cccctttgtc t                                               21

<210> SEQ ID NO 16
<211> LENGTH: 23
<212> TYPE: DNA
<213> ORGANISM: Artificial Sequence
<220> FEATURE:
<223> OTHER INFORMATION: Synthesized primer

<400> SEQUENCE: 16
agctaatgaa acctcgcaga tcc                                             23

<210> SEQ ID NO 17
<211> LENGTH: 23
<212> TYPE: DNA
<213> ORGANISM: Artificial Sequence
<220> FEATURE:
<223> OTHER INFORMATION: Synthesized primer
```

```
<400> SEQUENCE: 17
agctcaccag cctcatctgt ctc                                          23

<210> SEQ ID NO 18
<211> LENGTH: 22
<212> TYPE: DNA
<213> ORGANISM: Artificial Sequence
<220> FEATURE:
<223> OTHER INFORMATION: Synthesized primer

<400> SEQUENCE: 18
gtatgactcc actcacggca aa                                           22

<210> SEQ ID NO 19
<211> LENGTH: 20
<212> TYPE: DNA
<213> ORGANISM: Artificial Sequence
<220> FEATURE:
<223> OTHER INFORMATION: Synthesized primer

<400> SEQUENCE: 19
ggtctcgctc ctggaagatg                                              20
```

LACTIC ACID BACTERIA AND ITS APPLICATIONS IN IMMUNOMODULATION AND ANTI-INFLAMMATION

FIELD OF THE INVENTION

The invention relates to a probiotic and a composition comprising the same. Particularly, the invention relates to a new lactic acid bacteria and its use in enhancing immunomodulatory and anti-inflammatory activity.

BACKGROUND OF THE INVENTION

Fermented food products contain various useful bacteria, including lactic acid bacteria (LAB). Various strains of LAB are used in the manufacture of fermented foods, including milk, bread, vegetables, and other edible plant materials. LAB is a group of Gram-positive bacteria generally used in the production of fermented foods. The benefits of LAB in dietary and clinical applications have been widely studied. LAB have been utilized as fermenting agents for the preservation of food taking benefit of a low pH and the action of fermentation products generated during the fermentative activity thereof to inhibit the growth of spoilage bacteria. To this end, LAB have been used for preparing a variety of different foodstuff such as cheese, yogurt and other fermented dairy products from milk. It has attracted a great deal of attention in that LAB have been found to exhibit valuable properties to man and animals upon ingestion. In particular, specific strains of the genus *Lactobacillus* or *Bifidobacterium* have been found to be able to colonize the intestinal mucosa and to assist in the maintenance of the well-being of man and animal. Anti-inflammatory activity and the immunomodulatory activity are well-known characteristic of LAB.

WO 97/00078 discloses a specific strain, named as *Lactobacillus* GG (ATCC 53103), which is a probiotic. The microorganism in WO 97/00078 is particularly employed in a method of preventing or treating food induced hypersensitivity reactions. U.S. Pat. No. 8,361,481 provides a lactic acid bacterium having an anti-allergic activity, which is a lactic acid bacterium *Lactobacillus paracasei* K71 strain which has been internationally deposited in National Institute of Advanced Industrial Science and Technology, International Patent Organism Depositary under Accession No. FERM BP-11098. L. Zhang et al. reports the effect of *Lactobacillus rhamnosus* GG in decreasing inflammation (*Journal of Pediatric Gastroenterology and Nutrition*, vol. 42, no. 5, pp. 45-52, 2006). Also, several prior art references have reported that Lactic acid bacteria inhibit proinflammatory cytokine expression (for example, *World Journal of Gastroenterology*, vol. 16, no. 33, pp. 4145-4151, 2010; and *International Immunopharmacology*, vol. 8, no. 4, pp. 574-580, 2008).

The growth metabolic products of *Lactobacillus plantarum* KFCC11389P inhibited the production of TNF-α and IL-6 in LPS-treated RAW 264.7 cells. *Lactobacillus plantarum* 10hk2 has been shown to exhibit immunomodulatory effects by increasing the production of pro-inflammatory mediators, such as interleukin-1β (IL-1β), IL-6 and TNF-α, and the anti-inflammatory mediator interleukin-10 (IL-10) in RAW 264.7 cells.

However, the effectiveness of LAB is variable due to the properties and capabilities of different strains. Therefore, there is a need to develop a LAB with advantageous immunomodulatory and anti-inflammatory activity.

SUMMARY OF THE INVENTION

The invention provides a new LAB strain with immunomodulatory and anti-inflammatory activity and a composition containing and method using the same. The LAB of the invention can be administrated for modulating an immune response in order to restore or prevent metabolic disorders caused by obesity or chronic inflammation.

The invention provides an isolated LAB, which is *Lactobacillus plantarum* subsp. *plantarum* having 16S rRNA gene and pheS gene containing the nucleic acid sequences as shown in the following SEQ ID NO: 1 and SEQ ID NO:2, respectively. In one embodiment, the LAB of the invention is *Lactobacillus plantarum* subsp. *plantarum* K21, deposited on Jun. 27, 2013 with DSMZ-DEUTSCHE SAMMLUNG VON MIKROORGANISMEN UND ZELLKULTUREN (DSMZ) (located at Inhoffenstraβe 7B, 38124 Braunschweig, Germany) under accession number DSM 27444.

K21 is a probiotic strain isolated from fu-tsai, a Taiwanese traditional fermented food. The pheS sequence of K21 shows highest similarity to *Lactobacillus plantarum* subsp. *plantarum* and may represent a new species within the genus *Lactobacillus*. K21 shows significant inhibition on TNF-α and prostaglandin $E_2$ ($PGE_2$) productions, suggesting that K21 exhibits anti-inflammatory activity. K21 also reduces the production of pro-inflammatory cytokines and the mRNA expression levels of TNF-α, cyclooxygenase 2 (COX-2), toll like receptor 4 (TLR4), and suppressor of cytokine signaling 3 (SOCS3) in vivo.

The invention also provides a composition comprising the LAB of the invention and optionally an edible carrier. In another further aspect, the invention provides a method of enhancing immunomodulatory and/or anti-inflammatory activity, comprising administering the lactic acid bacteria or a composition of the invention to a subject.

DETAILED DESCRIPTION OF THE INVENTION

Figure 1:
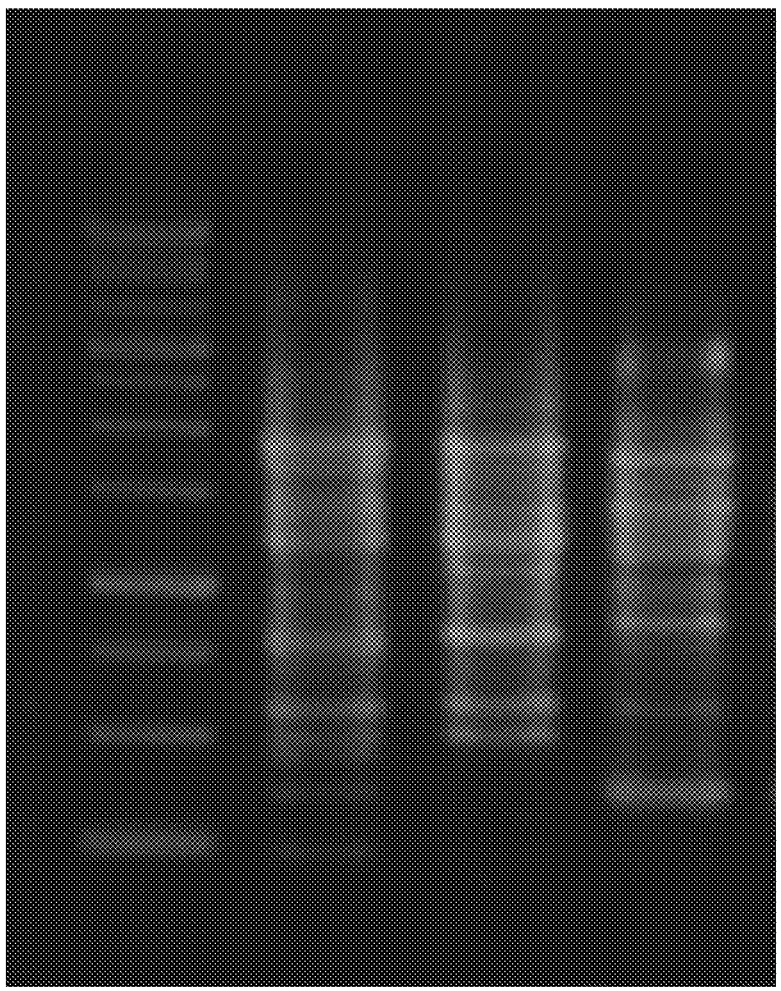
FIG. 1 show a set of electrophoresis photographs showing the RAPD profiles of three *Lactobacillus plantarum* strains. Lane M, 1 kb DNA ladders; 1, *Lactobacillus plantarum* subsp. *plantarum* K21; 2, *Lactobacillus plantarum* subsp. *plantarum* ATCC 14917$^T$; 3, *Lactobacillus plantarum* subsp. *argentoratensis* ATCC 17638$^T$.

The invention surprisingly found a new LAB strain with immunomodulatory and anti-inflammatory activity. The LAB of the invention can be administrated for modulating an immune response in order to restore or prevent metabolic disorders caused by obesity or chronic inflammation.

The term "probiotic" is recognized in the state of the art as a microorganism which, when administered in adequate amounts, confers a health benefit to the host. A probiotic microorganism must fulfil several requirements related to lack of toxicity, viability, adhesion and beneficial effects. These probiotic features are strain-dependent, even among bacteria of the same species.

The term "pharmaceutically acceptable" as used herein refers to compounds, materials, compositions, and/or dosage forms which are, within the scope of sound medical judgment, suitable for use in contact with the tissues of a subject (either a human or non-human animal) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation. Suitable carriers, excipients, etc. can be found in standard pharmaceutical texts.

The term "edible carrier" refers to compounds, materials, compositions, and/or dosage forms which are, suitable for use in contact with the tissues of a subject. Each carrier must also be "acceptable" in the sense of being compatible with the other ingredients of the formulation.

The term "effective amount" as used herein is the amount of colony forming units (cfu) for each strain in the composition that is high enough to significantly modify the condition to be treated in a positive way but low enough to avoid serious side effects (at a reasonable benefit/risk ratio), within the scope of sound medical judgment.

In one aspect, the invention provides an isolated LAB, which is *Lactobacillus plantarum* subsp. *plantarum* having 16S rRNA gene and pheS gene containing the nucleic acid sequences as shown in the following SEQ ID NO:1 and SEQ ID NO:2, respectively.

```
                                              SEQ ID NO: 1
GGAGACTATACATGCAAGTCGAACGAACTCTGGTATTGATTGGTGCTTGC

ATCATGATTTACATTTGAGTGAGTGGCGAACTGGTGAGTAACACGTGGGA

AACCTGCCCAGAAGCGGGGGATAACACCTGGAAACAGATGCTAATACCGC

ATAACAACTTGGACCGCATGGTCCGAGTTTGAAAGATGGCTTCGGCTATC

ACTTTTGGATGGTCCCGCGGCGTATTAGCTAGATGGTGGGGTAACGGCTC

ACCATGGCAATGATACGTAGCCGACCTGAGAGGGTAATCGGCCACATTGG

GACTGAGACACGGCCCAAACTCCTACGGGAGGCAGCAGTAGGGAATCTTC

CACAATGGACGAAAGTCTGATGGAGCAACGCCGCGTGAGTGAAGAAGGGT

TTCGGCTCGTAAAACTCTGTTGTTAAAGAAGAACATATCTGAGAGTAACT

GTTCAGGTATTGACGGTATTTAACCAGAAAGCCACGGCTAACTACGTGCC

AGCAGCCGCGGTAATACGTAGGTGGCAAGCGTTGTCCGGATTTATTGGGC

GTAAAGCGAGCGCAGGCGGTTTTTTAAGTCTGATGTGAAAGCCTTCGGCT

CAACCGAAGAAGTGCATCGGAAACTGGGAAACTTGAGTGCAGAAGAGGAC

AGTGGAACTCCGTGTGTAGCGGTGAAATGCGTAGATATATGGAAGAACAC

CAGTGGCGAAGGCGGCTGTCTGGTCTGTAACTGACGCTGATGCTCGAAAG

TATGGGTAGCAAACAGGATTAGATACCCTGGTAGTCCATACCGTAACGAT

GAATGCTAAGTGTTGGAGGGTTTCCGCCCTTCAGTGCTGCAGCTAACGCA
```

```
                                              -continued
TTAAGCATTCCGCCTGGGGAGTACGGCGCAGGCTGAAACTCAGAGGAATT

GACGGGGGTCCCGCACAAGCGGTGCAGCATGTGTTTATTCGAAGCTACGC

GAAGATCTACAGGTCTGACATACTATGCAAATCTAGAAATAACGTTCTTT

CGTGACATGCATACAGTGTGCATGGTGTCGTCAGTCAGTTCCTGATGTCG

ATTAGTTCAAGACGAGGCACCTACTATCAGTGCCAGCATAGTGGCATCTG

TGAGACTGCCGTGACAAAC
```

```
                                              SEQ ID NO: 2
TGCGAATATTACCAAGACGTGCTACTACGCACGCAGACGTCTGCTGATCA

GCCGCGGTCACTTGAAAATCACGATTTTTCTAAAGGACCGCTGAAGGTCT

TGTCACCTGGCCGCGTTTATCGGCGTGATACGGATGATGCAACCCATTCC

CATCAATTTCATCAAATTGAAGGGTTAGTCGTGGACAAGCATATTACGAT

GGCTGATTTGAAGGGCACCTTAATTCTGGTTGCCAAGACTTTGTTTGGCG

ATCAATTCGATGTTCGGCTACGGCCAAGCTTCTTTCCATTCACGGAACCA

TCCGTAGAAGCTGATGTAACTTGCTTTAATTGCAATGGCAAGGGCTGTGC

AATCTGTAAGCAAACGGGTTGGATCGAAGTACTGGGTGCCGGCATGGTTC

ACCCCCACGTGTTAGAAATGTCTGGCATTGATCCAGAAGAATATGGTGGC

TTTGCTTTCGGGGTCTTGGAACA.
```

In one embodiment, the LAB of the invention is *Lactobacillus plantarum* subsp. *plantarum* K21, deposited with DSMZ-DEUTSCHE SAMMLUNG VON MIKROORGANISMEN UND ZELLKULTUREN (DSMZ) under accession number DSM 27444.

The new LAB of the invention is named as *Lactobacillus plantarum* subsp. *plantarum* K21, which has been deposited with DSMZ-DEUTSCHE SAMMLUNG VON MIKROORGANISMEN UND ZELLKULTUREN GmbH (Inhoffenstr. 7 B, D-38124 Braunschweig, Germany) on Jun. 27, 2013 under Budapest Treaty and was given the DSMZ Accession No. DSM 27444.

*Lactobacillus plantarum* subsp. *plantarum* K21 (K21) is a probiotic strain isolated from fu-tsai, a Taiwanese traditional fermented food. The 16S rRNA gene and pheS gene sequences of K21 shows highest similarity to *Lactobacillus plantarum* subsp. *plantarum*, but are different from it. Consequently, K21 represents a new strain of *Lactobacillus plantarum* subsp. *plantarum*.

The fermentation test indicates that K21 harbor a biochemical property similar to *Lactobacillus plantarum* subsp. *plantarum*. K21 exhibits positive to the following: L-arabinose, D-ribose, D-xylose, D-galactose, D-glucose, D-fructose, D-mannose, L-rhamnose, D-mannitol, D-sorbitol, methyl-α-D-mannopyranoside, N-acetyl glucosamine, amygdalin, arbutin, esculin ferric citrate, salicin, D-cellobiose, D-maltose, D-lactose, D-melibiose, D-saccharose (sucrose), D-trehalose, inulin, D-melezitose, D-raffinose, gentiobiose, D-turanose, D-tagatose and potassium gluconate, but negative to the following: glycerol, erythritol, D-arabinose, L-xylose, D-adonitol, methyl-β-D-xylopyranoside, L-sorbose, dulcitol, inositol, methyl-α-D-glucopyranoside, amidon (starch), glycogen, xylitol, D-lyxose, D-fucose, L-fucose, D-arabitol, L-arabitol, potassium 2-ketogluconate and potassium 5-ketogluconate.

K21 shows significant inhibition on TNF-α and prostaglandin $E_2$ ($PGE_2$) productions, suggesting that K21 exhibits anti-inflammatory activity. K21 reduces the production of pro-inflammatory cytokines such as TNF-α, IL-1β, and IL-6 in vivo. Also, K21 reduces the mRNA expression levels of TNF-α, cyclooxygenase 2 (COX-2), toll like receptor 4 (TLR4), and suppressor of cytokine signaling 3 (SOCS3) in vivo.

In another aspect, the invention provides a composition comprising the LAB of the invention and optionally an edible carrier. In another further aspect, the invention provides a method of enhancing immunomodulatory and/or anti-inflammatory activity, comprising administering the LAB or a composition of the invention to a subject.

In the compositions of the invention, said strain can be used in the form of whole bacteria which may be living or not. Preferably the bacterial cells are present as living, viable cells.

The compositions of the invention can be in any form suitable for administration, in particular oral administration. This includes for instance solids, semi-solids, liquids, and powders.

The composition can for example comprise at least $10^5$ cfu, preferably at least $10^6$ cfu, per g dry weight, of the strains of LAB as mentioned above.

When the LAB are in the form of living bacteria, the composition may typically comprise $10^5$ to $10^{13}$ colony forming units (cfu), preferably at least $10^6$ cfu, more preferably at least $10^7$ cfu, still more preferably at least $10^8$ cfu, and most preferably at least $10^9$ cfu per g dry weight of the composition.

Examples of the compositions of the invention are nutritional compositions, including food products and in particular dairy products.

The composition can be for example a capsule, tablet, drink, powder or dairy product. Optionally, other strains of LAB may be present. Preferably the present nutritional composition is a baby food, an infant milk formula or an infant follow-on formula. Preferably the present composition is a nutraceutical or a pharmaceutical product, a nutritional supplement or medical food.

Nutritional compositions of the invention also include food supplements, and functional food. A "food supplement" designates a product made from compounds usually used in foodstuffs, but which is in the form of tablets, powder, capsules, potion or any other form usually not associated with aliments, and which has beneficial effects for one's health. A "functional food" is an aliment which also has beneficial effects for one's health. In particular, food supplements and functional food can have a physiological effect—protective or curative—against a disease, for example against a chronic disease.

If the composition according to the invention is a dietary supplement, it can be administered as such, can be mixed with a suitable drinkable liquid, such as water, yoghurt, milk or fruit juice, or can be mixed with solid or liquid food. In this context the dietary supplement can be in the form of tablets, pills, capsules, lozenges, granules, powders, suspensions, sachets, pastilles, sweets, bars, syrups and corresponding administration forms, usually in the form of a unit dose. Preferably, the dietary supplement comprising the composition of the invention is administered in the form of tablets, lozenges, capsules or powders, manufactured in conventional processes of preparing dietary supplements.

The present invention is described in greater detail by the examples presented below, which are preceded by a brief description of the figures. It goes without saying however, that these examples are given by way of illustration of the subject of the invention and do not constitute in any manner a limitation thereto. The percentages are given by weight unless otherwise stated.

EXAMPLE

Example 1 Isolation and Genetic Typing of *Lactobacillus plantarum* Subsp. *Plantarum* K21

K21 was isolated from fu-tsai, a Taiwanese traditional fermented food. The 16S rRNA gene and pheS gene DNA from K21 was analyzed by direct sequencing of PCR-amplified DNA fragments.

PCR was carried out under the condition indicated in below Table using the 16S rRNA gene primers (Bact-8F(II): 5'-AGAGTTTGATCMTGGCTCAG-3' (SEQ ID NO:3); 15R: 5'-AAGGAG GTGATCCAACCGCA-3' (SEQ ID NO:4) or pheS primers (pheS-Forward: 5'-CAYCCNGCH-CGYGAYATGC-3' (SEQ ID NO:5); pheS-Reverse: 5'-CCWARVCCRAARGCAAARCC-3' (SEQ ID NO:6). The resulting sequence was put into the alignment software provided online by the National Center for Biotechnology Information (NCBI) (http://www.ncbi.nlm.nih.gov/), aligned manually and compared with representative pheS DNA sequences of organisms belonging to the Firmicutes. For comparison, 16S rRNA gene and pheS DNA sequences were also obtained from the database provided online by the NCBI.

As a result of this analysis, the following Table 1 lists those organisms, whose pheS DNA sequences show the highest similarity values compared to the pheS DNA sequence of K21.

TABLE 1

Comparison Between 16S rRNA Gene (A) and pheS (B) Sequences (A)

| Strain (GenBank accession number) | % 16S rRNA gene sequence similarity to K21 |
|---|---|
| *Lactobacillus pentosus* (D79211) | 100 |
| *Lactobacillus plantarum* subsp. *plantarum* (D79210) | 99.8 |
| *Lactobacillus paraplantarum* (AJ306297) | 99.6 |
| *Lactobacillus plantarum* subsp. *argentoratensis* (AJ640078) | 99.0 |
| *Lactobacillus collinoides* (AB005893) | 92.6 |
| *Lactobacillus brevis* (M58810) | 92.4 |
| *Lactobacillus buchneri* (AB205055) | 90.5 |
| *Lactobacillus fermentum* (M58819) | 89.1 |

(B)

| Strain (GenBank accession number) | pheS gene sequence similarity to K21 (%) |
|---|---|
| *Lactobacillus plantarum* subsp. *plantarum* (AM087714) | 99.7 |
| *Lactobacillus plantarum* subsp. *argentoratensis* (AM694185) | 91.1 |
| *Lactobacillus paraplantarum* (AM087727) | 89.9 |
| *Lactobacillus brevis* (AM087680) | 66.7 |
| *Lactobacillus collinoides* (AM087730) | 66.4 |
| *Lactobacillus buchneri* (AM087681) | 65.6 |
| *Lactobacillus fermentum* (AM087693) | 63.5 |
| *Lactobacillus pentosus* (AM087713) | 58.4 |

The comparison of 16S rRNA gene indicates that K21 belong to *Lactobacillus pentosus, Lactobacillus plantarum* subsp. *plantarum/argentoratensis*, or *Lactobacillus paraplantarum*, which is not distinguishable since all their similarity values are greater than 98%. Moreover, the combined result of sequence analysis of 16S rRNA gene and pheS of K21 shows highest similarity to *Lactobacillus plantarum* subsp. *plantarum*. Consequently, K21 represents a new strain of *Lactobacillus plantarum* subsp. *plantarum*.

TABLE 2

Composition of the PCR reaction solution (25 μl)

| Component | Volume |
| --- | --- |
| Molecular Biology Grade Water | 15.3 μl |
| 10x PCR buffer | 2.5 μl |
| dNTP (2.5 mM) | 2 μl |
| Forward primer (10 μM) | 2 μl |
| Reverse primer (10 μM) | 2 μl |
| TaKaRa Taq | 0.2 μl |
| Template DNA (10 ng/μl) | 1 μl |

PCR Conditions: 94° C., 5 min.; 35 cycles (94° C., 30 sec.; 55° C., 30 sec.; 72° C., 90 sec.; 72° C., 10 min.); 4° C., ∞.

```
Lactobacillus plantarum subsp. plantarum
K21 16S rRNA gene sequence (SEQ ID NO. 1):
GGAGACTATACATGCAAGTCGAACGAACTCTGGTATTGATTGGTGCTTGC

ATCATGATTTACATTTGAGTGAGTGGCGAACTGGTGAGTAACACGTGGGA

AACCTGCCCAGAAGCGGGGGATAACACCTGGAAACAGATGCTAATACCGC

ATAACAACTTGGACCGCATGGTCCGAGTTTGAAAGATGGCTTCGGCTATC

ACTTTTGGATGGTCCCGCGGCGTATTAGCTAGATGGTGGGGTAACGGCTC

ACCATGGCAATGATACGTAGCCGACCTGAGAGGGTAATCGGCCACATTGG

GACTGAGACACGGCCCAAACTCCTACGGGAGGCAGCAGTAGGGAATCTTC

CACAATGGACGAAAGTCTGATGGAGCAACGCCGCGTGAGTGAAGAAGGGT

TTCGGCTCGTAAAACTCTGTTGTTAAAGAAGAACATATCTGAGAGTAACT

GTTCAGGTATTGACGGTATTTAACCAGAAAGCCACGGCTAACTACGTGCC

AGCAGCCGCGGTAATACGTAGGTGGCAAGCGTTGTCCGGATTTATTGGGC

GTAAAGCGAGCGCAGGCGGTTTTTTAAGTCTGATGTGAAAGCCTTCGGCT

CAACCGAAGAAGTGCATCGGAAACTGGGAAACTTGAGTGCAGAAGAGGAC

AGTGGAACTCCGTGTGTAGCGGTGAAATGCGTAGATATATGGAAGAACAC

CAGTGGCGAAGGCGGCTGTCTGGTCTGTAACTGACGCTGATGCTCGAAAG

TATGGGTAGCAAACAGGATTAGATACCCTGGTAGTCCATACCGTAACGAT

GAATGCTAAGTGTTGGAGGGTTTCCGCCCTTCAGTGCTGCAGCTAACGCA

TTAAGCATTCCGCCTGGGGAGTACGGCGCAGGCTGAAACTCAGAGGAATT

GACGGGGGTCCCGCACAAGCGGTGCAGCATGTGTTTATTCGAAGCTACGC

GAAGATCTACAGGTCTGACATACTATGCAAATCTAGAAATAACGTTCTTT

CGTGACATGCATACAGTGTGCATGGTGTCGTCAGTCAGTTCCTGATGTCG

ATTAGTTCAAGACGAGGCACCTACTATCAGTGCCAGCATAGTGGCATCTG

TGAGACTGCCGTGACAAAC

Lactobacillus plantarum subsp. plantarum
K21 pheS gene sequence (SEQ ID NO. 2):
TGCGAATATTACCAAGACGTGCTACTACGCACGCAGACGTCTGCTGATCA

GCCGCGGTCACTTGAAAATCACGATTTTTCTAAAGGACCGCTGAAGGTCT

TGTCACCTGGCCGCGTTTATCGGCGTGATACGGATGATGCAACCCATTCC

CATCAATTTCATCAAATTGAAGGGTTAGTCGTGGACAAGCATATTACGAT

GGCTGATTTGAAGGGCACCTTAATTCTGGTTGCCAAGACTTTGTTTGGCG

ATCAATTCGATGTTCGGCTACGGCCAAGCTTCTTTCCATTCACGGAACCA

TCCGTAGAAGCTGATGTAACTTGCTTTAATTGCAATGGCAAGGGCTGTGC

AATCTGTAAGCAAACGGGTTGGATCGAAGTACTGGGTGCCGGCATGGTTC

ACCCCCACGTGTTAGAAATGTCTGGCATTGATCCAGAAGAATATGGTGGC

TTTGCTTTCGGGGTCTTGGAACA
```

Example 2 Identification of the Bacterial Strains Using RAPD-PCR

The RAPD profiles of K21 and other two *Lactobacillus plantarum* strains (ATCC 14917[T] and ATCC 17638[T]) were compared. PCR was carried out under the condition indicated in Table 3 using the random primer 1254 (5'-CCGCAGC-CAA-3', SEQ ID NO. 7). DNAs respectively extracted from these strains were used as templates. The obtained amplification products were electrophoresed and the patterns were compared as shown in FIG. 1. This result showed that K21 harbored a specific PCR-fingerprinting deduced from its genome, representing that K21 is a novel strain.

TABLE 3

Composition of the PCR reaction solution (25 μl)

| Component | Volume |
| --- | --- |
| ddH$_2$O | 17.9 μl |
| 10X PCR Buffer | 2.5 μl |
| dNTP Mix (2.5 mM) | 2.0 μl |
| MgCl$_2$ (25 mM) | 1.0 μl |
| primer | 0.4 μl |
| rTaq | 0.2 μl |
| DNA template (10 μM) | 1.0 μl |

PCR Conditions: 94° C., 2 min.; 5 cycles (94° C., 30 sec.; 36° C., 1 min.; 72° C., 1.5 min.); 30 cycles (94° C., 20 sec.; 36° C., 30 sec.; 72° C., 1.5 min.); 72° C., 3 min.

Example 3 Analytical Profile Index (API) Typing

Sugar utilization for K21 used in the present invention was investigated using API50CHL kit (bioMerieux, France), and the results are shown in Table 4. The fermentation test indicates that K21 harbor a biochemical property similar to *Lactobacillus plantarum* subsp. *plantarum*.

TABLE 4

Results of Fermentation Test[a]

| carbohydrates substrate | K21 (DSM 27444) |
| --- | --- |
| CONTROL | − |
| Glycerol | − |
| Erythritol | − |
| D-Arabinose | − |
| L-Arabinose | + |
| D-Ribose | + |
| D-Xylose | + |
| L-Xylose | − |
| D-Adonitol | − |
| Methyl-β-D-Xylopyranoside | − |
| D-Galactose | + |
| D-Glucose | + |
| D-Fructose | + |
| D-Mannose | + |

TABLE 4-continued

Results of Fermentation Test[a]

| carbohydrates substrate | K21 (DSM 27444) |
|---|---|
| L-Sorbose | − |
| L-Rhamnose | + |
| Dulcitol | − |
| Inositol | − |
| D-Mannitol | + |
| D-Sorbitol | + |
| Methyl-α-D-mannopyranoside | + |
| Methyl-α-D-glucopyranoside | − |
| N-Acetyl glucosamine | + |
| Amygdalin | + |
| Arbutin | + |
| Esculin ferric citrate | + |
| Salicin | + |
| D-Cellobiose | + |
| D-Maltose | + |
| D-Lactose (bovine origin) | + |
| D-Melibiose | + |
| D-Saccharose (sucrose) | + |
| D-Trehalose | + |
| Inulin | + |
| D-Melezitose | + |
| D-Raffinose | + |
| Amidon (starch) | − |
| Glycogen | − |
| Xylitol | − |
| Gentiobiose | + |
| D-Turanose | + |
| D-Lyxose | − |
| D-Tagatose | + |
| D-Fucose | − |
| L-Fucose | − |
| D-Arabitol | − |
| L-Arabitol | − |
| Potassium gluconate | + |
| Potassium 2-ketogluconate | − |
| Potassium 5-ketogluconate | − |

[a]+, positive; −, negative

Example 4 Preparation of *Lactobacillus plantarum* Subsp. *Plantarum* K21

K21 was inoculated in de Man, Rogosa, and Sharpe (MRS, pH 5.4; Difco, USA) broth and cultured at 30° C. for 21 hrs. For a live K21 preparation, the isolated bacteria was harvested using centrifugation for 10 min at 1500 g, then washed twice with sterile phosphate buffered saline (PBS), and then re-suspended to a final concentration of $1 \times 10^9$ CFU/mL. For a heat-killed K21 preparation, K21 were prepared to certain concentration as live K21 preparation procedure. Then, K21 were heat-killed at 100° C. for 20 min and were stored at −20° C. until use.

Example 5 TNF-α and PGE2 Production Inhibited by *Lactobacillus plantarum* Subsp. *Plantarum* K21

Preparation and Stimulation of RAW 264.7 Cells

Figure 2:
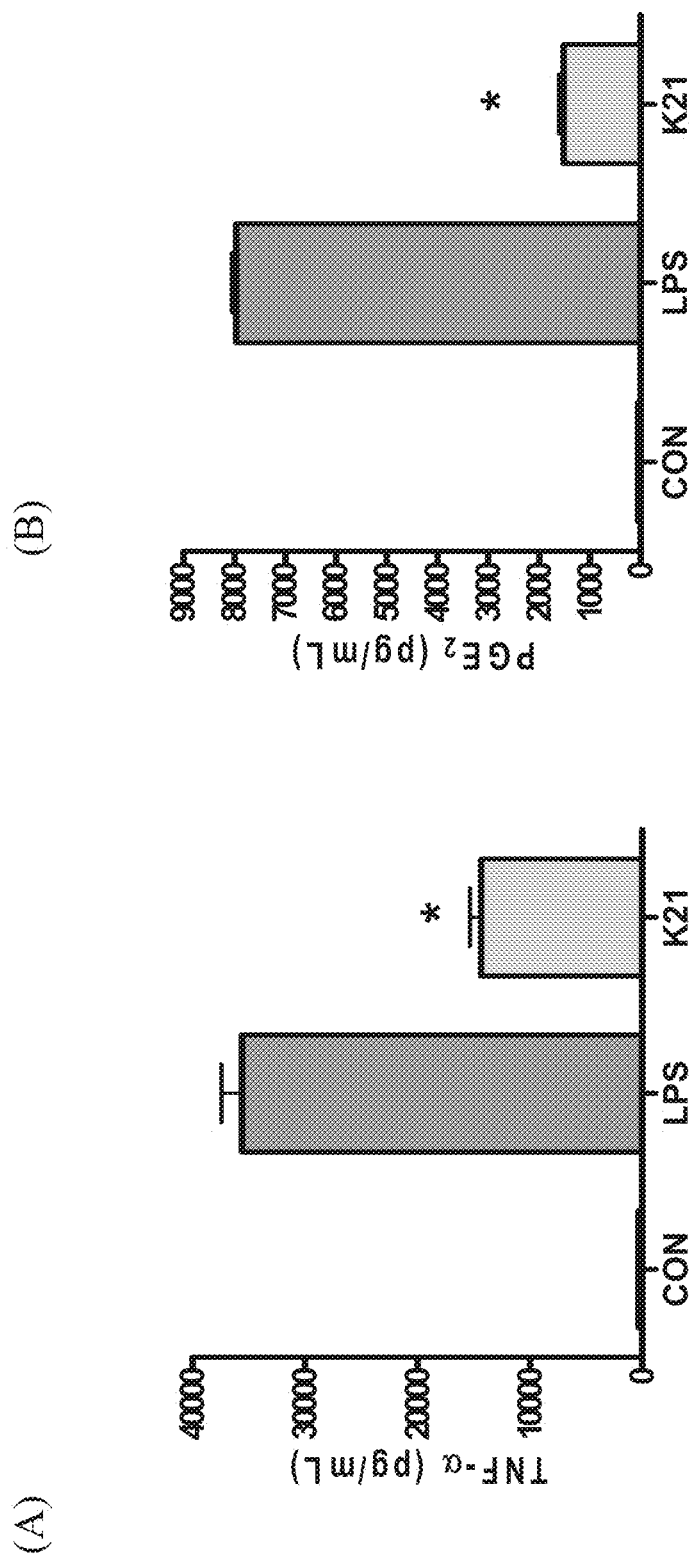
FIG. 2 show TNF-α and PGE2 production of normal RAW 264.7 cells, LPS-treated (20 hrs, 600 ng/mL) RAW 264.7 cells, and LPS-treated (20 hrs, 600 ng/mL) RAW 264.7 cells co-treated with heat-killed K21 ($1 \times 10^6$ CFU).

Murine macrophage RAW 264.7 cells were purchased from the American Type Culture Collection (ATCC; Manassas, Va., USA) and maintained in Dulbecco's modified Eagle's medium (DMEM; Gibco BRL, Grand Island, N.Y.) supplemented with 10% fetal bovine serum (FBS), 100 IU/ml penicillin, 0.1 mg/ml streptomycin, 0.25 μg/ml amphotericin, and 1% L-glutamate. The cells were cultured at 37° C. in 5% $CO_2$ incubator. RAW 264.7 were plated at a density of $1 \times 10^5$ cells/ml in 96-well plates for 24 hours and then stimulated with LPS (600 ng/ml) in the presence of heat-killed K21 ($1 \times 10^6$ cfu). The control experiments were performed with medium LPS as a positive control and medium only as a negative control. After 20 hours of incubation, supernatants were collected for TNF-α and $PGE_2$ concentrations assays. FIG. 2 shows that TNF-α and PGE2 production of normal RAW 264.7 cells, LPS-treated (20 hrs, 600 ng/mL) RAW 264.7 cells, and LPS-treated (20 hrs, 600 ng/mL) RAW 264.7 cells co-treated with heat-killed K21 ($1 \times 10^6$ CFU). The result showed that the treatment of K21 attenuated the elevated production of TNF-α and PGE2 in macrophage in response to LPS, indicating an anti-inflammatory activity harbored by K21.

Example 6 In Vivo Immune and Inflammatory Assays for *Lactobacillus plantarum* Subsp. *Plantarum* K21

Experimental Animals and Grouping

Five-week-old female BALB/c mice were purchased from the National Laboratory Animal Center (NLAC; Taipei, Taiwan). Mice were housed in filter-top cages in a specific pathogen-free room under standard conditions (22° C., 50-60% humidity, and 12 hours light/dark cycle) with free access to standard mouse/rat chow diet (LabDiet Autoclavable Rodent Diet 5010, PMI Nutrition International, Brentwood, Mo.) and water. After one week acclimatization to laboratory conditions, mice were separated into three groups: health control group, ulcerative colitis (UC) control group and UC+K21 group. Health control group and UC control group were administered vehicle alone (0.2 ml PBS) from day 1 to day 14, while the UC+K21 group was oral administered K21 ($1 \times 10^9$ cfu in 0.2 ml PBS). The drinking water of the UC and UC+K21 groups was replaced with 5% dextran sodium sulfate (DSS) in water from day 8 to day 14.

*Lactobacillus plantarum* Subsp. *Plantarum* K21 Attenuates Weight Loss and Colon Shortening in Dextran Sodium Sulfate (DSS)-Induced Mouse Ulcerative Colitis (UC)

The oral administration of DSS can induce acute UC symptoms in BALB/c mice, including weight loss, bloody diarrhea, colonic mucosal inflammation and colon shortening.

Weight change and colon length of the healthy control (Health control), UC control, and K21 groups on day 14. Weight change=Mouse weight on day 14−mouse weight on day 1. The colon length was measured from ileocecal junction to anus. The data are expressed as the mean±S.D., with n=8 mice for each group. A difference between comparison groups was considered statistically significant when $p<0.05$ (*). a, UC control and UC+K21 groups compared with the healthy control group; b, UC+K21 group compared with UC control group. These results showed a significant weight loss and colon length shortening in the UC group, compared with that in the healthy group, and these symptoms could be attenuated by the oral administration of K21.

| | | Health Control | UC control | K21 |
|---|---|---|---|---|
| K21 | Weight change (g) | 1.9 ± 0.7 | −1.1 ± 0.7*[a] | −0.3 ± 0.9*[a,b] |
| | Colon length (cm) | 9.0 ± 0.6 | 6.0 ± 0.6*[a] | 6.5 ± 0.5*[a,b] |

Figure 3:
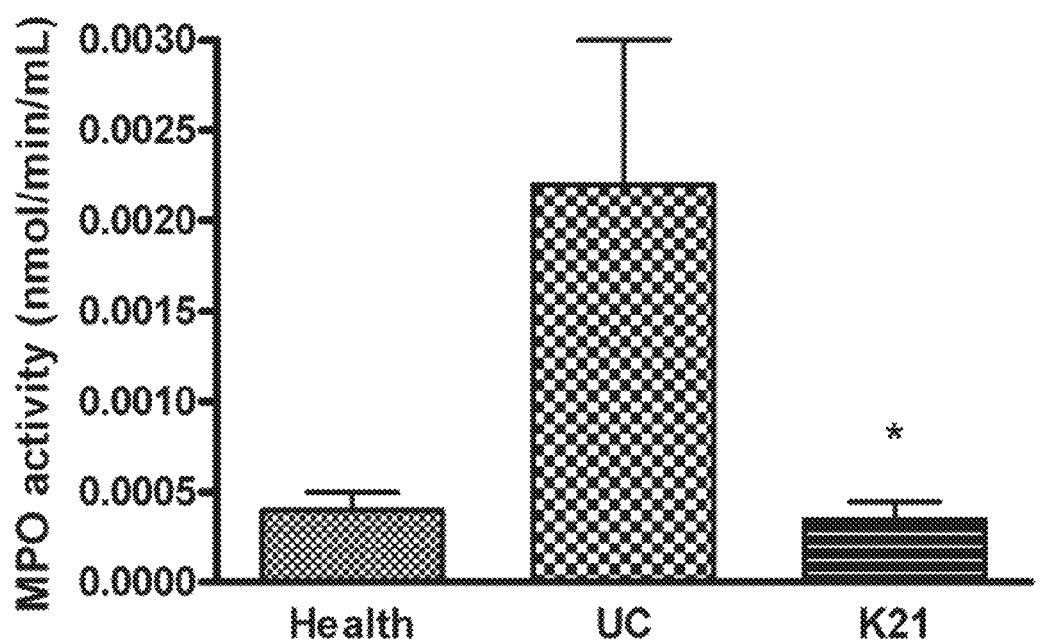
FIG. 3 shows that the MPO activities of colonic proteins of the healthy control (Health), UC control (UC), and K21 groups were assessed. The data are expressed as the mean±S.D., with n=6 mice for each group. A difference between K21 and UC groups was considered statistically significant when p<0.05 (*).

MPO is a member of the heme peroxidase superfamily and is stored within the azurophilic granules of leukocytes. MPO has been found within circulating neutrophils, monocytes, and some tissue macrophages. MPO-derived oxidants also contribute to tissue damage and the initiation and propagation of acute and chronic vascular inflammatory diseases. DSS treatment has been shown to significantly increase colonic MPO activity in experimental animals. The MPO activities of colonic proteins of the healthy control (Health), UC control (UC), and K21 groups were assessed. The data are expressed as the mean±S.D., with n=6 mice for each group. A difference between K21 and UC groups was considered statistically significant when p<0.05 (*). FIG. 3 shows that decreased MPO activity represented moderate neutrophil infiltration in the UC+K21 group compared with the UC control group, indicating an in vivo anti-inflammatory activity harbored by K21.

Measurement of Immunoglobulins and Cytokines

Figure 4:
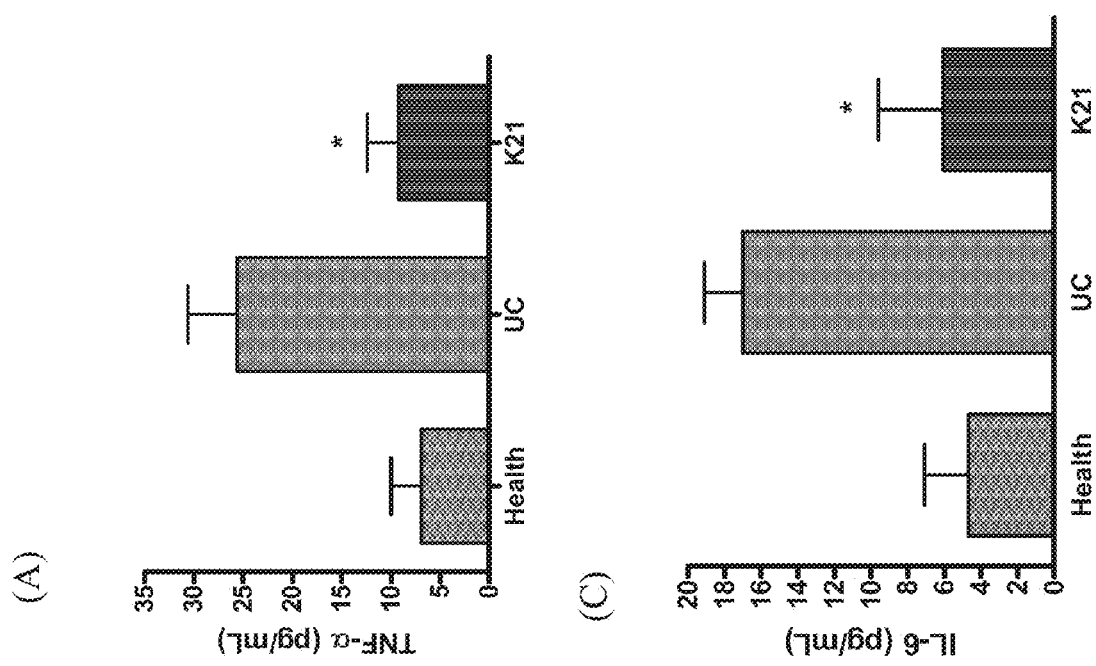
FIG. 4 (A)~(C) show the effects of oral administration of live K21 ($1 \times 10^9$ CFU) on TNF-α (A), IL-1β (B), and IL-6 (C) concentrations in colonic total protein in UC mouse model, compared with UC control group.

The concentrations of TNF-α, IL-1β, IL-6, IFN-γ, IL-10, and $PGE_2$ were determined using ELISA procedure according to the manufacturers' instructions (for TNF-α, IL-1β, and IL-6, eBioscience, Boston, Mass.; for IFN-γ and IL-10, R&D Systems, Minneapolis, Minn.; for $PGE_2$, Cayman Chemical, Ann Arbor, Mich.). For colonic tissue cytokine determination, 100 μg of protein from each colon sample was used. The level of colonic cytokines was determined and expressed as pg of cytokine/mg of colonic protein (pg/mg). FIG. 4 (A)~(C) show the effects of oral administration of live K21 ($1\times10^9$ CFU) on TNF-α (A), IL-1β (B), and IL-6 (C) concentrations in colonic total protein in UC mouse model, compared with UC control group. The result indicated that the DSS treatment caused elevated productions of the inflammatory cytokines, TNF-α, IL-1β, and IL-6, which could be attenuated by oral administration of K21.

Example 7 Quantitative Real-Time RT-PCR for Gene Expression Analysis

Total RNA from each mouse colon was prepared using the RNeasy mini kit (Qiagen GmbH, Hilden, Germany), and cDNA was then synthesized using an oligo(dT)$_{15}$ primer and SuperScript™ II reverse transcriptase reagents (Life Technologies, Carlsbad, Calif.). Quantitative real-time PCR was performed in a LightCycler instrument (Roche Diagnostics, Mannheim, Germany) using the DyNAmo Capillary SYBR Green qPCR kit (Finnzymes, Espoo, Finland) according to the manufacturer's recommendations. The fluorescence signal was detected at the end of each cycle. The results were analyzed using the LDCA software supplied with the machine, and a melting curve was used to confirm the specificities of the products. The expression levels of target mRNAs of each sample were normalized to GAPDH as an internal control. Results were expressed as relative expression ratios to the healthy control group. All primers used were showing at Table 5.

TABLE 5

Primer Sets for the Real-Time RT-PCR

| Gene name | Primer sequence | Size (bp) | Accession no. |
|---|---|---|---|
| TNF-α | F: GTGGAACTGGCAGAAGAGGC (SEQ ID NO. 8) R: AGACAGAAGAGCGTGGTGGC (SEQ ID NO. 9) | 122 | NM_013693.2 |
| TLR-4 | F: AGGAGTGCCCCGCTTTCACC (SEQ ID NO. 10) R: TGCCAGAGCGGCTGCCAGA (SEQ ID NO. 11) | 203 | NM_021297.2 |
| COX-2 | F: GAAGTCTTTGGTCTGGTGCCTG (SEQ ID NO.12) R: GTCTGCTGGTTTGGAATAGTTGC (SEQ ID NO. 13) | 133 | NM_0111983 |
| Foxp3 | F: TGCAGGGCAGCTAGGTACTTGTA (SEQ ID NO. 14) R: TCTCGGAGATCCCCTTTGTCT (SEQ ID NO. 15) | 123 | NM_001199347.1 |
| SOCS3 | F: AGCTAATGAAACCTCGCAGATCC (SEQ ID NO. 16) R: AGCTCACCAGCCTCATCTGTCTC (SEQ ID NO. 17) | 97 | NM_007707.3 |
| GAPDH | F: GTATGACTCCACTCACGGCAAA (SEQ ID NO. 18) R: GGTCTCGCTCCTGGAAGATG (SEQ ID NO. 19) | 101 | NM_008084 |

* F: forward primer; R: reverse primer.

Figure 5:
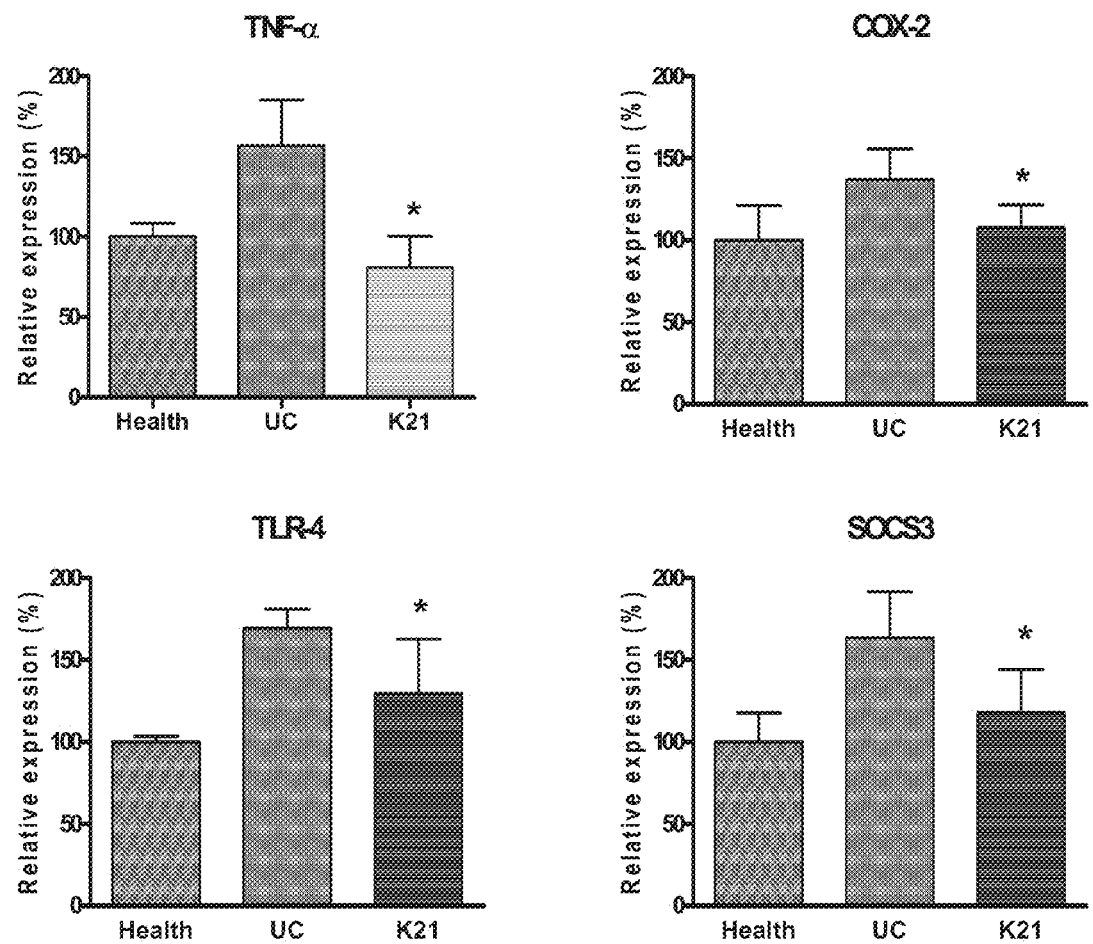
FIG. 5 show the effects of oral administration of live K21 ($1 \times 10^9$ CFU) on the mRNA expression levels of TNF-α, COX-2, TLR4, and SOCS3 in the colon of UC mouse model, compared to healthy control group, UC control group. The mRNA expression levels were examined using real-time PCR.

All data presented herein were expressed as means±the standard deviation (SD). The differences between means were tested for statistical significance using a one-way ANOVA followed by a Tukey's post-hoc test. Differences between the control group and other groups were considered statistically significant when the P<0.05 (*) or <0.01 (**). FIG. 5 show the effects of oral administration of live K21 ($1\times10^9$ CFU) on the mRNA expression levels of TNF-α, COX-2, TLR4, and SOCS3 in the colon of UC mouse model, compared with UC control group. The mRNA expression levels were examined using real-time PCR. The result indicated that the DSS treatment caused elevated mRNA expression levels of TNF-α, COX-2, TLR4, and SOCS3, which could be attenuated by oral administration of K21, indicating that K21 exerted in vivo immunomodulation.

What is claimed is:

1. A method of enhancing immunomodulatory and/or anti-inflammatory activity, comprising administering the lactic acid bacteria of the a composition comprising an isolated lactic acid bacteria and an edible carrier to a subject, wherein the isolated lactic acid bacteria is *Lactobacillus plantarum* subsp, *plantarum* having 16S rRNA gene and pheS gene containing the nucleic acid sequences as shown in the SEQ ID NO: 1 and SEQ ID NO: 2; wherein the isolated lactic acid bacteria is *Lactobacillus plantarum* subsp, *plantarum* K21, deposited with DSMZ-DEUTSCHE SAMMLUNG VON MIKROORGANISMEN UND ZELLKULTUREN (DSMZ) under accession number DSM 27444.

2. The method of claim 1, wherein the isolated lactic acid bacteria is *Lactobacillus plantarum* subsp. *plantarum* K21, deposited with DSMZ-DEUTSCHE SAMMLUNG VON MIKROORGANISMEN UND ZELLKULTUREN (DSMZ) under accession number DSM 27444.

3. The method of claim 1, wherein the isolated lactic acid bacteria is heat-killed bacteria.

4. The method of claim 1, wherein the isolated lactic acid bacteria is present at least 105 cfu per g dry weight of the strains of *Lactobacillus plantarum* subsp. *plantarum*.

5. The method of claim 1, wherein the isolated lactic acid bacteria exhibits positive to the following: L-arabinose, D-ribose, D-xylose, D-galactose, D-glucose, D-fructose, D-mannose, L-rhamnose, D-mannitol, D-sorbitol, methyl-α-D-mannopyranoside, N-acetyl glucosamine, amygdalin, arbutin, esculin ferric citrate, salicin, D-cellobiose, D-maltose, D-lactose, D-melibiose, D-saccharose (sucrose), D-trehalose, inulin, D-melezitose, D-raffinose, gentiobiose, D-turanose, D-tagatose and potassium gluconate, but negative to the following: glycerol, erythritol, D-arabinose, L-xylose, D-adonitol, methyl-β-D-xylopyranoside, L-sorbose, dulcitol, inositol, methyl-α-D-glucopyranoside, amidon (starch), glycogen, xylitol, D-lyxose, D-fucose, L-fucose, D-arabitol, L-arabitol, potassium 2-ketogluconate and potassium 5-ketogluconate.

6. The method of claim 1, wherein the isolated lactic acid bacteria inhibits TNF-α and prostaglandin E2 (PGE2) productions.

7. The method of claim 1, wherein the isolated lactic acid bacteria exhibits anti-inflammatory activity.

8. The method of claim 1, wherein the isolated lactic acid bacteria reduces the production of pro-inflammatory cytokine selected from TNF-α, IL-1β, and IL-6.

9. The method of claim 1, wherein the isolated lactic acid bacteria reduces the mRNA expression levels of TNF-α, cyclooxygenase 2 (COX-2), toll like receptor 4 (TLR4), and/or suppressor of cytokine signaling 3 (SOCS3).

* * * * *